US 6,971,792 B2

(12) United States Patent
de Ris et al.

(10) Patent No.: US 6,971,792 B2
(45) Date of Patent: Dec. 6, 2005

(54) DEVICE AND METHOD FOR MEASURING ABSORBED HEAT FLUX IN A FIRE TEST APPARATUS

(75) Inventors: John L. de Ris, Foxborough, MA (US); Mohammed M. Khan, Sharon, MA (US)

(73) Assignee: FM Global Technologies LLC, Johnston, RI (US)

( * ) Notice: Subject to any disclaimer, the term of this patent is extended or adjusted under 35 U.S.C. 154(b) by 0 days.

(21) Appl. No.: 10/681,175

(22) Filed: Oct. 9, 2003

(65) Prior Publication Data

US 2005/0078732 A1  Apr. 14, 2005

(51) Int. Cl.[7] .......................... G01K 17/00; G01K 7/02
(52) U.S. Cl. .............................. 374/29; 374/32; 374/1; 374/5; 374/179; 73/866.4
(58) Field of Search ........................... 374/29, 30, 179, 374/43, 32, 45, 57, 5, 4, 1, 12; 73/866.4

(56) References Cited

U.S. PATENT DOCUMENTS

| | | | | |
|---|---|---|---|---|
| 2,769,334 A | * | 11/1956 | Soehngen | 374/43 |
| 3,088,072 A | * | 4/1963 | Clifford et al. | 374/32 |
| 3,431,149 A | * | 3/1969 | Robinson et al. | 136/213 |
| 3,765,238 A | * | 10/1973 | Sumikama et al. | 374/30 |
| 3,819,419 A | * | 6/1974 | Loose | 136/213 |
| 4,309,901 A | * | 1/1982 | Rolinski et al. | 374/29 |
| 4,906,105 A | * | 3/1990 | Geake | 374/30 |
| 5,161,889 A | * | 11/1992 | Smith et al. | 374/29 |
| 6,568,846 B1 | * | 5/2003 | Cote et al. | 374/5 |

* cited by examiner

Primary Examiner—Gail Verbitsky
Assistant Examiner—Stanley J. Pruchnic, Jr.
(74) Attorney, Agent, or Firm—Merek, Blackmon & Voorhees, LLC

(57) ABSTRACT

A device for measuring the flux received by a specimen in fire test apparatuses has a copper disk or plate of the same dimensions and the same type of surface coating as a typical material specimen, an embedded heating coil and thermocouple, and an insulated sample holder similar to that used for a specimen. The transient response of the embedded thermocouple is measured for several different levels of imposed incident radiation without electrical heating and for several different known levels of electrical heating without any imposed radiation. The principle of Electrical Substitution Radiometry (ESR) is applied, and the transient responses to incident radiation and electrical heating under identical thermal conditions are compared to determine the amount of incident radiation that is actually absorbed by the device while it is being irradiated. The situations are kept thermally identical, thereby insuring that all effects due to heat losses (e.g. convection, radiation and conduction) are exactly the same.

10 Claims, 6 Drawing Sheets

DEVICE AND METHOD FOR MEASURING ABSORBED HEAT FLUX IN A FIRE TEST APPARATUS

BACKGROUND OF THE INVENTION

Test apparatuses approved by ASTM International, Inc. for measuring the fire hazard of materials or objects, such as the Cone Calorimeter and the Fire Propagation Apparatus, irradiate a specimen of a material or an object with a known infrared (IR) heat flux from a radiant heating source. The specimen is typically coated with paint or a carbon mixture to improve absorption of the radiant heat flux in order to simulate heat absorption during an actual fire, when the material or object becomes covered with soot and thereby absorbs most of the radiant energy incident upon it. The purpose of the test is to determine, for example, when the specimen material or object, such as an electrical component, ignites, becomes inoperative or begins to vaporize. The fire test apparatuses employ radiant heaters to simulate the heating by a fire.

The incident heat flux from the radiant heater is often taken as a measure of the heat flux required to cause the detectable condition or response, such as ignition, of the material or object. However, because of the coating, not all of the heat flux incident on the coating is absorbed by the specimen, and the portion of the heat flux emanating from radiant heating source that is absorbed by the specimen varies from one coating to another. As a result, there is a problem evaluating and comparing test data from specimens having different coatings.

In addition to the problem that the portion of the incident heat flux that is absorbed by the specimen varies from coating to coating, the present inventors have found that absorption of radiant heat flux by most surfaces including typical applied coatings significantly decreases for flux incident at oblique or glancing angles in fire test apparatuses. In order to interpret test results from different test apparatuses, which are often in different laboratories and in which different coatings may be used and/or in which the angle of incidence of the radiant heat flux may vary, the heat flux absorbed by the specimen must be known, as opposed to the heat flux incident on the coating. However, prior to the present invention, there was no standard device or method for measuring the heat flux actually absorbed by a specimen in a fire test apparatus. For the purpose of determining the fire hazard of a material, the absorbed flux, rather than the incident flux, is of primary concern.

SUMMARY OF THE INVENTION

By the present invention, the measurement of heat flux absorbed by a specimen becomes apparatus-independent. In other words, the test data from specimens that have different coatings and/or are tested in different test apparatuses can be equalized and compared. For each coating in each test apparatus, a device according to the present invention measures the IR heat flux absorbed or received by an object relative to the IR heat flux incident on the coating of the object. More specifically, a copper disk having an imbedded electrical heating coil, a thermocouple for measuring the temperature of the disk, and a surface area similar to that of the specimen being tested is situated in a typical specimen holder. The disk has an exposed surface that is coated with the same coating as is applied to the specimen. Then, the principle of absolute Electrical Substitution Radiometry (ESR) is applied to the device.

According to ESR one determines the radiant flux (optical power per unit area) $\Phi$ that is actually absorbed by a receiving surface (or object). The receiving surface (or object) is coupled to a constant temperature heat sink at a reference temperature, $T_0$. Following the onset of imposed radiation, the surface (or object) will experience a transient temperature rise, $T(t)-T_0$, at time t after imposition of radiation. The temperature rise generally depends on both time and magnitude of the received flux, $\Phi$. This is expressed by the function, $G(t, \Phi)$ namely, $T(t)-T_0=G(t, \Phi)$. A similar temperature rise, $T(t)-T_0$, would occur if, instead of imposing a radiant flux, $\Phi$, one applied an electrical power, P per unit area, to the surface (or object). The two temperature rises will be identical at the same time interval, t, following imposition of heat, if $P=\Phi$. By finding the power P per unit area that gives exactly the same transient temperature rise, as a radiant flux, $\Phi$, one successfully determines the radiant flux, $\Phi$.

It is quite convenient to measure electrical power as a substitute for measuring a radiant flux. Electrical power can be measured rather accurately. The advantage of using ESR is that it overcomes possible measurement errors due to heat losses from the surface, (e.g. convection, surface radiation, conduction, etc). By reproducing the temperature rise, one insures that the heat losses are the same for both the imposed radiant flux, $\Phi$, and electrical power per unit area, P. Indeed, the technique provides a convenient, accurate and reliable method for calibrating the radiant heaters of the fire test apparatus. It is an absolute (i.e. primary) method of calibration of the radiant heaters irradiating a specimen having a defined surface coating. It depends solely on one's ability to measure the electrical power P that reproduces the measured temperature rise.

In accordance with the present invention, the principle of ESR is applied to the device in connection with testing of specimen materials or objects to determine the heat flux involved in causing the specimen to ignite, become inoperative, begin to vaporize or exhibit some other characteristic in response. More specifically, for low heat fluxes, the coated disk is exposed to a heat flux from a radiant heat source, such as an IR heating apparatus, until the thermocouple records a steady-state temperature, where the heat absorbed by the disk is equal to the heat losses given off by the disk. Subsequently, with no incident radiant heat flux on the coated disk, the IR heating is reduced to zero, and an electrical power of sufficient magnitude is supplied to the imbedded electrical heating coil for the disk to return to the same steady-state temperature. Electrical power used by the electrical heating coil to return the disk to the same steady-state temperature is equal to the total heat absorbed by the disk in the IR heating apparatus. The electrical power can be accurately measured. In a test apparatus in which the angle of incidence is set, the specimen, which has the same coating as the disk, as well as the same coated surface area and same insulation as the disk, receives the same heat flux as the disk. This application of absolute electrical substitution radiometry (ESR) can be performed for various levels of incident flux, supplied electrical power supply, and steady-state disk temperature.

It has been found that it is not even necessary to reach a steady-state temperature. Instead, a rate of rise in the temperature of the disk due to the radiant heating can be duplicated by the rate of rise in the temperature of the disk due to electrical heating. Then, the power required to achieve that rate by the radiant heating is compared with the power required to achieve that rate by the electrical heating. The method of duplicating the rate of rise of the temperature

BRIEF DESCRIPTION OF THE DRAWING FIGURES

FIG. 3b is a graph showing the rise in temperature at identical time $t_1$ taken from the curves shown in FIG. 3a.

DETAILED DESCRIPTION OF THE PREFERRED EMBODIMENT

Figure 1:
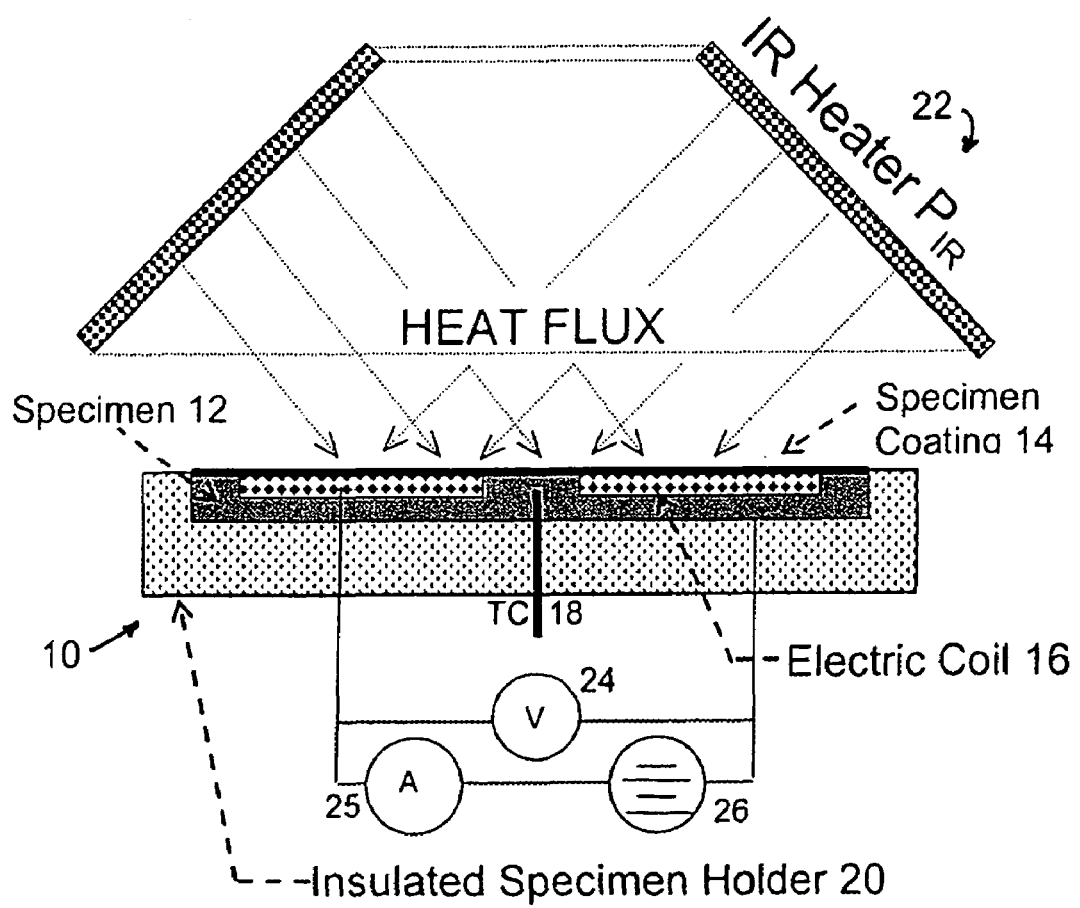
FIG. 1 is a schematic illustration of a device according to the present invention for measuring absorbed heat flux positioned under a radiant heating apparatus in a fire hazard test apparatus.

As can be seen from FIG. 1, a device for determining the radiant heat flux received by a test specimen having a coating to improve the absorption of the radiant heat flux, which is designated generally by the reference numeral 10, has a body 12, and a coating 14 on the body, the coating on the body being the same as the coating on the test specimen. The device 10 also has an electrical heating element 16 in heat transfer relationship with the body 12, such that the coating 14 is not interposed between the heating element and the body. A thermal detector, such as a thermocouple 18 connected to the body 12, for indicating the temperature of the body is also a part of the device 10. The body 12 is a metal disk of, for example, copper, and the electrical heating element can be an electric resistance heating element and can be positioned within the body.

The device 10 further includes an insulated holder 20 for the body 12, wherein the body has a first surface to which the coating 14 is applied and at least one other surface, the first surface being exposed for receiving radiant heat flux from a radiant heating source, such as a radiant heating apparatus 22. The radiant heating apparatus 22 can be conical in shape and can be a part of a conventional Cone Calorimeter or Fire Propagation Apparatus. The body 12 also has a bottom surface and a side surface, both of which can be covered by heat insulating material of the insulated holder 20. The insulated holder 20 is the same as the insulated holder used for specimens that are tested in connection with the device 10 according to the present invention.

In order to indicate the electrical power applied to the electrical heating element 16, a voltmeter 24 and an ammeter 25 are electrically connected to the electrical heating element 16 to measure the power applied to the electrical heating element by an electrical power source 26.

The device 10 according to the present invention is made as similar as possible to a specimen to be tested and its holder. With the exception of the electrical heating element 16, the thermocouple 18, the voltmeter 24, the ammeter 25, the electrical power source 26 and the material of the body 12, the specimen and its insulated holder are the same as the device 10. In particular, the area of the specimen and of the body 10 exposed to radiant heating is the same, the coatings are the same, and the insulated holder is the same. The body 12 is coated to simulate the heat absorption characteristics of a material or device in a fire. The same is done with the specimens of the material or device.

Figure 2A:
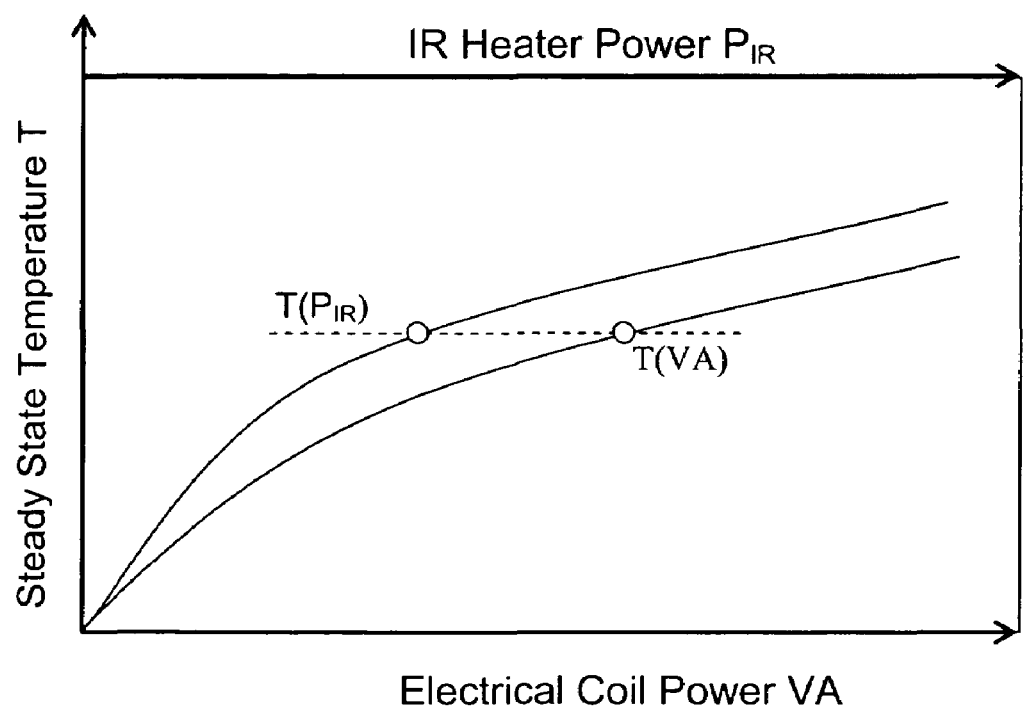
FIG. 2a is a graph showing the measured steady state temperature of a device according to the present invention versus the power required from IR heaters, $P_{IR}$, with no power applied to the electrical coil (i.e. VA=0) and versus the power delivered to the electrical coil heater VA with zero power applied to the IR heaters (i.e. $P_{IR}$=0)
Figure 2B:
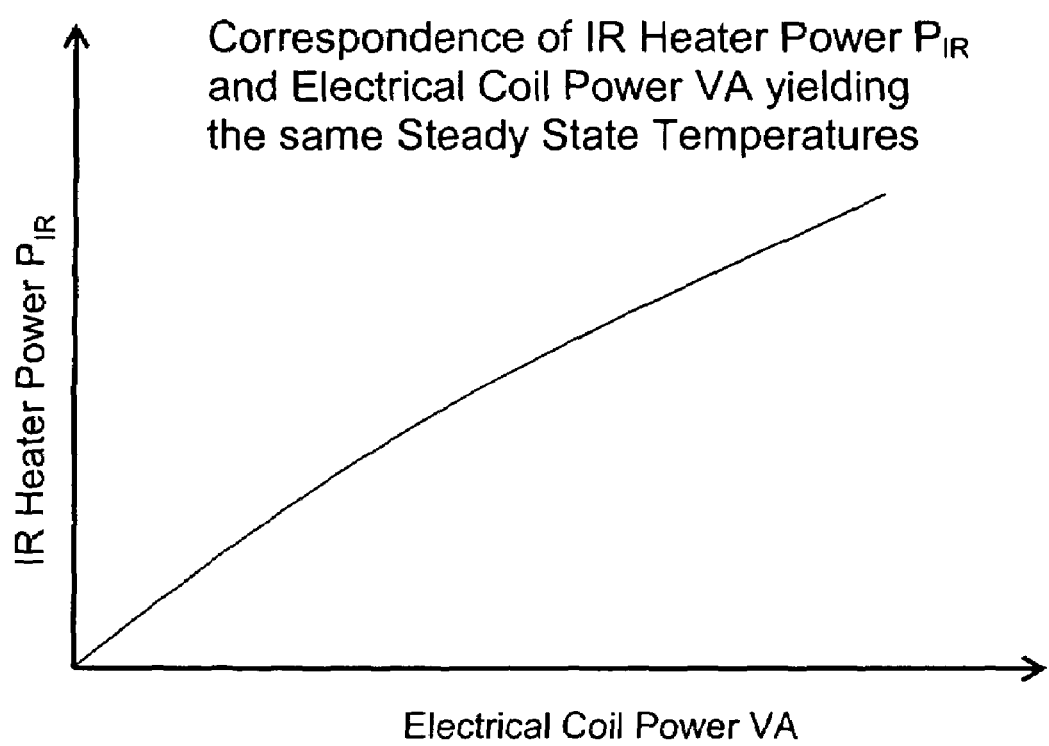
FIG. 2b is a graph, generated from the data of FIG. 2a, showing the IR heater power $P_{IR}$ providing the same steady state temperatures as that obtained with electrical coil power VA.

Radiation from the radiant heating apparatus 22 is applied to the measuring device 10 through the coating 14 to heat the measuring device to a steady-state temperature. The IR heating is reduced to zero, and sufficient power is applied to the electrical heating element 16 of the measuring device 10 for the body 12 to reach the steady-state temperature. Using the readings on the voltmeter 24 and the ammeter 25 and the duration of the period required to reach the steady-state temperature, the power required for reaching the steady-state temperature by using the electrical heating element 16 can be calculated and compared with the power required for reaching the same steady-state temperature by using the radiant heating apparatus 22. See FIGS. 2a and 2b.

It has been found that it is not even necessary to reach a steady-state temperature. Instead, the rate of rise in the temperature of the disk due to the radiant heating can be duplicated by the rate of rise in the temperature of the disk due to electrical resistance heating. Then, the power required to achieve that rate of the radiant heating is compared with the power required to achieve that rate by the electrical heating. The method of duplicating the rate of rise of the temperature of the disk is especially helpful for high heat fluxes, where the steady-state temperature of the disk is likely to be at a level at which the disk or other part of the device would be damaged. See FIGS. 3a and 3b.

In duplicating these rates of rise, several values of constant power $P_{IR}$ are applied to the radiant heating apparatus 22, yielding heat fluxes of approximately, for example, 20, 35 and 50 kW per square meter applied to the surface of the device 10. In each case, the temperature of the thermocouple 18 is recorded versus the time from the first moment of application of heat, as in FIG. 3a. This is done for several values of power $P_{IR}$ applied to the radiant heating apparatus 22, with zero power applied to the electrical coil 16 (i.e. VA=0). Then, the experiment is repeated, but with electrical power VA applied to the coil 16 and no power applied to the radiant heating or apparatus 22 (i.e., $P_{IR}$=0). The temperature rise versus time is recorded for these several values of electrical power VA with PR=0, as in FIG. 3a.

Figure 3A:
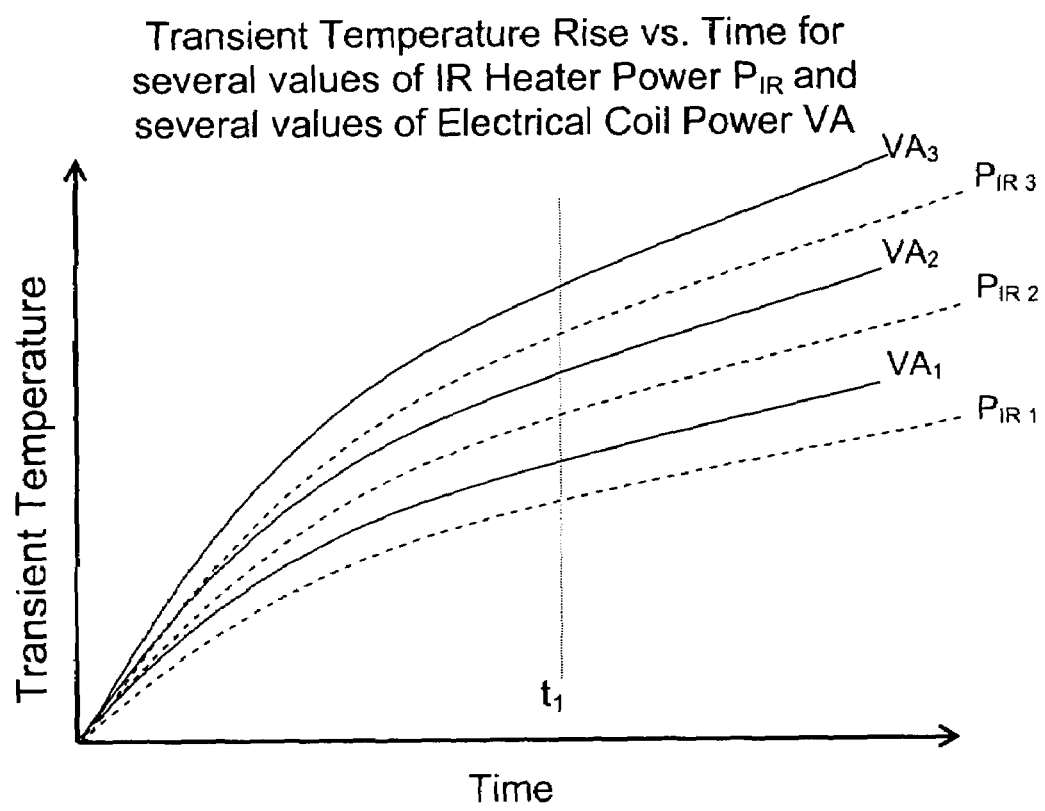
FIG. 3a shows the transient temperature rise for various levels of power applied only to the radiant heaters and only to the electrical coil.
Figure 3B:
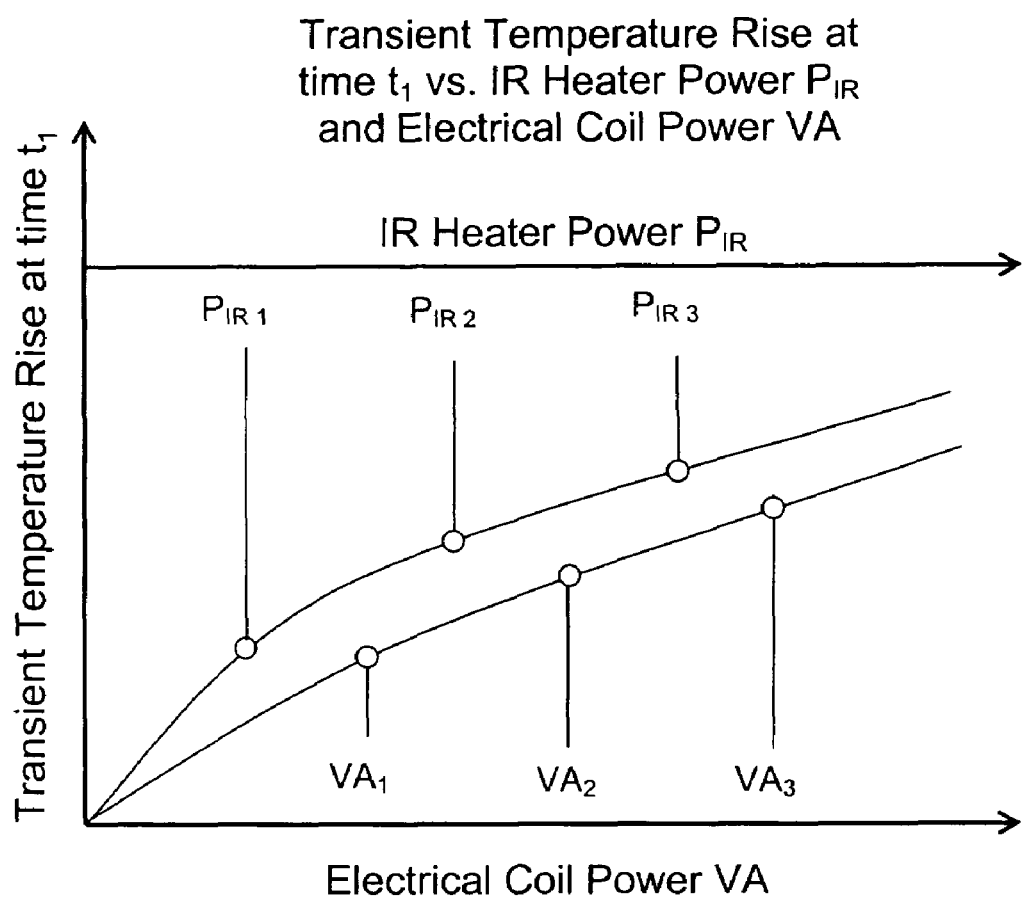
Figure 3C:
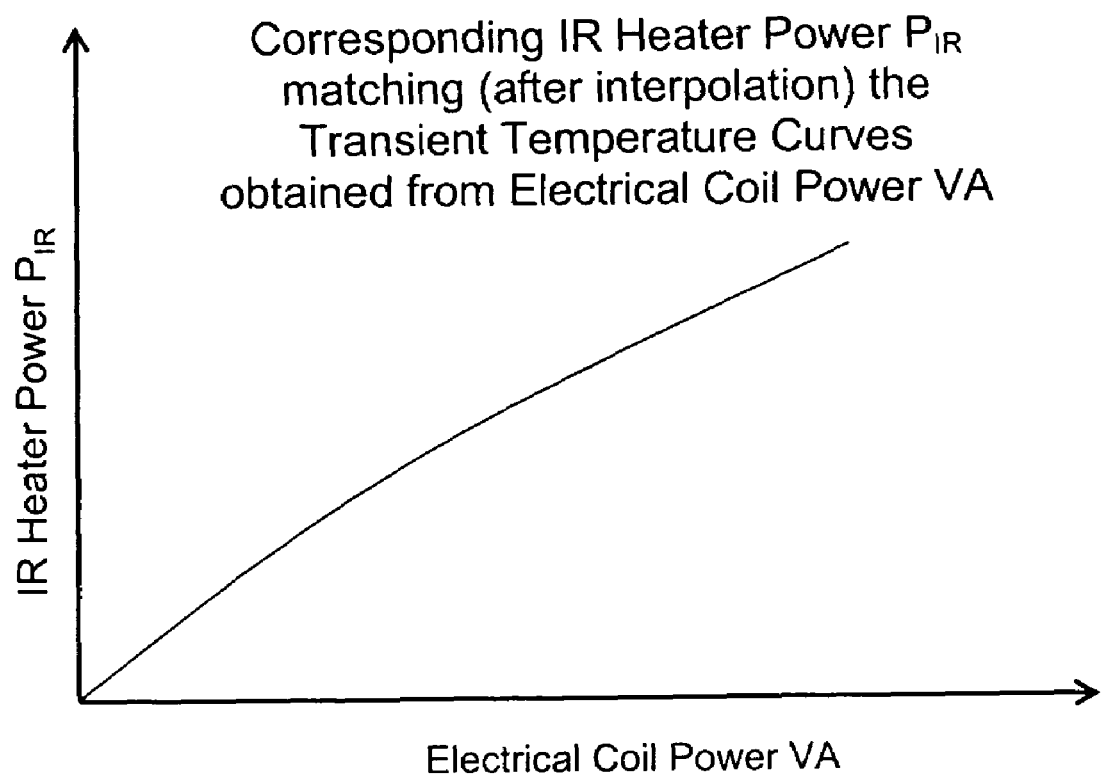
FIG. 3c shows the IR heater power, $P_{IR}$, that provides the same temperature rise at time $t_1$ as that provided by electrical coil power VA.

The temperature rises shown in FIG. 3a are compared at some selected time, for example, at $t_1$=60 seconds, after the beginning of the application of power to the radiant heating apparatus 22 and the electrical coils 16. These temperature rises are plotted, as in FIG. 3b, and smooth curves are drawn through the plotted points. Thus, FIG. 3a shows the transient temperature vs. time for several values of IR heater power $P_{IR}$ (with VA=0) and several values of electrical power VA (with $P_{IR}$=0). The applied power levels are compared for the values of temperature rise in a manner similar to that done for the steady temperatures shown in FIG. 2a to yield finally the correspondence between power $P_{IR}$ applied to the radiant heating device 22 and the power VA applied to the electrical coils 16, which can be plotted, as in FIG. 3c. Thus, the data shown by FIG. 3c is taken from FIG. 3b. By comparing the two sets of curves, one determines the radiant heat flux that is actually absorbed by the surface coating for various settings of the radiant heating device 22. The measurement takes into full account the effects of heat loss and the coating, as well as angles of incidence.

The embodiment illustrated and discussed in this specification is intended only to teach those skilled in the art the best way known to the inventors to make and use the invention. Nothing in this specification should be considered as limiting the scope of the present invention. The above-described embodiments of the invention may be modified or varied, and elements added or omitted, without departing from the invention, as appreciated by those skilled in the art in light of the above teachings. It is therefore to be understood that, within the scope of the claims and their equivalents, the invention may be practiced otherwise than as specifically described.

What is claimed is:

1. A measuring device for determining the radiant heat flux absorbed by a test specimen in a fire test apparatus, the specimen having an area exposed to radiant heating and being held in a specimen holder and coated with a coating to simulate the heat absorbtion of a material or object during a fire, comprising:
    a body;
    a coating on said body, the coating on said body being the same as the coating on the test specimen;
    a holder for said body that is the same as the specimen holder in which the specimen is held;
    an electrical heating element in heat transfer relationship with said body, free from interposition, between the heating element and said body, of the coating on said body; and
    a thermal detector indicating the temperature of the body.

2. The measuring device of claim 1, wherein said body has an area exposed to radiant heating that is the same as the area of the specimen that is exposed to radiant heating.

3. The measuring device of claim 2, wherein said body is made of copper.

4. The measuring device of claim 2, wherein said body is a metal disk.

5. The measuring device of claim 1, wherein the electrical heating element is positioned within said body.

6. The measuring device of claim 1, wherein the electrical heating element is an electric resistance heating element.

7. The measuring device of claim 1, wherein the thermal detector is a thermocouple connected to said body.

8. The measuring device of claim 1, further comprising an insulated holder for said body, wherein said body has a first surface to which the coating is applied and at least one other surface, said first surface being exposed for receiving radiant heat flux, and said other surface being covered by the insulated holder.

9. The measuring device of claim 1, further comprising means for indicating the electrical power applied to the electrical heating element.

10. A measuring device for determining the radiant heat flux absorbed by a test specimen in a fire test apparatus, the specimen having an area exposed to radiant heating and being held in a specimen holder and coated with a coating to simulate the heat absorption of a material or object during a fire, comprising:
    a body;
    a coating on said body, the coating on said body being the same as the coating on the test specimen;
    a holder for said body that is the same as the specimen holder in which the specimen is held:
    an electrical heating means in heat transfer relationship with said body, free from interposition, between the heating means and said body, of the coating on said body; and
    means for indicating the temperature of the body.

* * * * *